(12) United States Patent
Tajima et al.

(10) Patent No.: US 10,253,307 B2
(45) Date of Patent: Apr. 9, 2019

(54) PROTECTIVE STRUCTURE OF SUBSTANCE TO BE PROTECTED, METHOD OF PROTECTING SUBSTANCE TO BE PROTECTED, ENZYMATIC REACTION METHOD, METHOD OF PRODUCING REACTION PRODUCT, METHOD FOR ADJUSTING THE SPEED OF ENZYMATIC REACTION, AND ENZYME MATERIAL USE KIT

(71) Applicant: KANAGAWA UNIVERSITY, Kanagawa (JP)

(72) Inventors: Kazuo Tajima, Kanagawa (JP); Yoko Imai, Kanagawa (JP)

(73) Assignee: KANAGAWA UNIVERSITY, Kanagawa (JP)

( * ) Notice: Subject to any disclaimer, the term of this patent is extended or adjusted under 35 U.S.C. 154(b) by 0 days.

(21) Appl. No.: 13/919,557

(22) Filed: Jun. 17, 2013

(65) Prior Publication Data
US 2013/0288314 A1 Oct. 31, 2013

Related U.S. Application Data

(63) Continuation of application No. PCT/JP2011/079310, filed on Dec. 19, 2011.

(30) Foreign Application Priority Data

Dec. 17, 2010 (JP) ................................. 2010-282275

(51) Int. Cl.
| | | |
|---|---|---|
| C12N 9/96 | (2006.01) | |
| C07K 14/47 | (2006.01) | |
| C12N 9/26 | (2006.01) | |
| C12N 9/64 | (2006.01) | |

(52) U.S. Cl.
CPC ............ *C12N 9/96* (2013.01); *C07K 14/4732* (2013.01); *C12N 9/2414* (2013.01); *C12N 9/6472* (2013.01); *C12Y 302/01001* (2013.01); *C12Y 304/22002* (2013.01)

(58) Field of Classification Search
CPC ...... C12N 9/00; C12N 9/2414; C12N 9/6472; C12Y 304/22002; C12Y 302/01001; C07K 14/4732
USPC .................................................. 435/108, 187
See application file for complete search history.

(56) References Cited

U.S. PATENT DOCUMENTS

| | | | |
|---|---|---|---|
| 6,225,372 B1 | 5/2001 | Lykke et al. | |
| 2002/0106511 A1 | 8/2002 | Callisen | |
| 2007/0261293 A1 | 11/2007 | Tajima et al. | |

FOREIGN PATENT DOCUMENTS

| | | |
|---|---|---|
| JP | 58006530 A | 1/1983 |
| JP | 6-303973 A | 11/1994 |
| JP | 10-7587 A | 1/1998 |
| JP | H10158152 A | 6/1998 |
| JP | 2000-503052 A | 3/2000 |
| JP | 2001179077 A | 7/2001 |
| JP | 2003-164754 A | 6/2003 |
| JP | 2006239666 A | 9/2006 |
| JP | 3855203 B2 | 12/2006 |
| JP | 2007-77178 A | 3/2007 |
| JP | 2009-532566 A | 9/2009 |
| JP | 2010-110685 A | 5/2010 |
| WO | 2007/120547 A1 | 10/2007 |

OTHER PUBLICATIONS

Saeki et al., Microfluidic preparation of water-in-oil-in water emulsions with an ultra-thin oil phase layer. Lab on a Chip, vol. 10 (online Nov. 26, 2009) pp. 357-362.*
Mun et al., Preparation and characterization of water/oil/water emulsions stabilized by polyglycerol polyricinoleate and whey protein isolate. Journal of Food Science, vol. 75, No. 2 (Jan. 11, 2010) pp. E116-E125.*
Yamada et al., Spontaneous transfer of phospholipid-coated oil-in-oil and water-in-oil micro-droplets through and oil/water interface. Langmuir, vol. 22 (2006) pp. 9824-9828.*
Garti, N., Double emulsions-scope, limitations and new achievements. Colloids and Surfaces A: Physicochemical and Engineering Aspects, vol. 123-124 (1997) pp. 233-246.*
Extended European Search Report issued to EP Application No. 11848548.1, dated Apr. 22, 2014.
Ding Yingying et al: "A water-dispersible, ferrocene-tagged peptide nanowire for amplified electrochemical immunosensing", Biosensors & Bioelectronics, vol. 48, Jun. 6, 2007 (Jun. 6, 2007), pp. 281-286, XP002722501.
Walde P et al: "Enzymes inside lipid vesicles: preparation, reactivity and applications", Biomolecular Engineering, Elsevier, New York, NY, US, vol. 18, No. 4, Oct. 31, 2001 (Oct. 31, 2001), pp. 143-177, ISSN: 1389-0344, DOI: 10.1016/S1389-0344(01)00088-0.
European Patent Office Action corresponding to Application No. 11848548.1-1404; dated Sep. 7, 2015.

* cited by examiner

*Primary Examiner* — Kara D Johnson
(74) *Attorney, Agent, or Firm* — Cantor Colburn LLP

(57) ABSTRACT

Disclosed are a structure and a method capable of protecting from outside stimuli while containing in a liquid state a water-dispersible substance to be protected. The protective structure of the substance to be protected is a water-in-oil emulsion structure comprising an aqueous phase configuring a discontinuous phase containing the water-dispersible substance to be protected, an oil phase in which said aqueous phase is dispersed, and either vesicles formed with an amphiphilic substance which spontaneously forms vesicles or polycondensation polymer particles having hydroxyl groups.

13 Claims, 9 Drawing Sheets

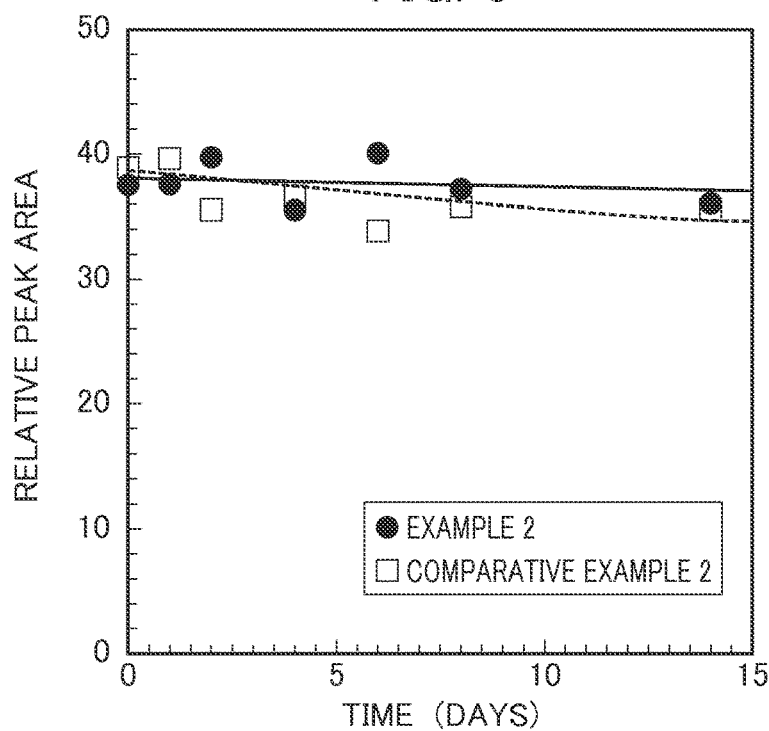
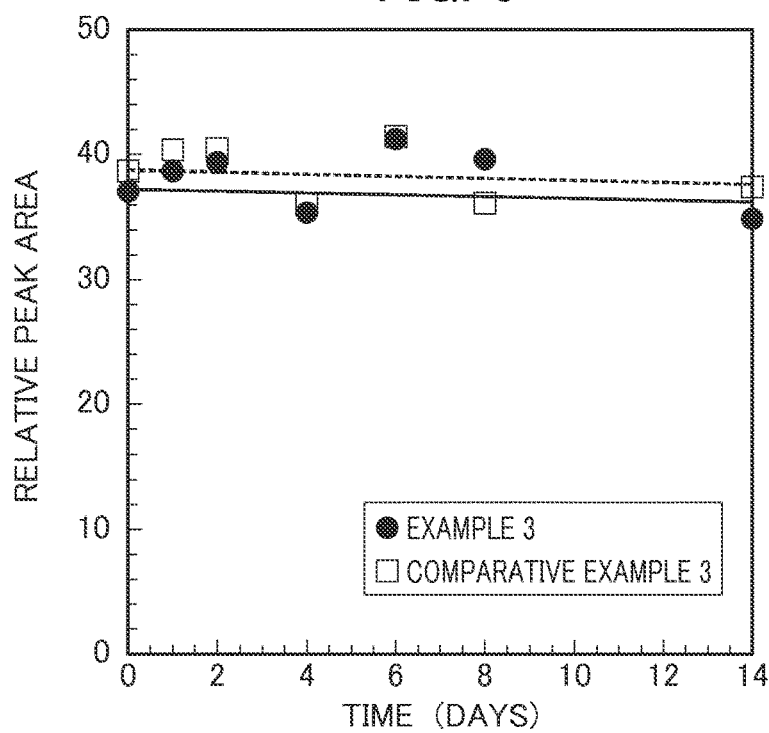

AQUEOUS SOLUTION SYSTEM

PROTECTIVE STRUCTURE OF SUBSTANCE TO BE PROTECTED, METHOD OF PROTECTING SUBSTANCE TO BE PROTECTED, ENZYMATIC REACTION METHOD, METHOD OF PRODUCING REACTION PRODUCT, METHOD FOR ADJUSTING THE SPEED OF ENZYMATIC REACTION, AND ENZYME MATERIAL USE KIT

CROSS REFERENCE TO RELATED APPLICATIONS

This application is a continuation under 35 U.S.C. § 120 of PCT/JP2011/079310, filed Dec. 19, 2011, which is incorporated herein reference and which claimed priority to Japanese Application No. 2010-282275, filed Dec. 17, 2010. The present application likewise claims priority under 35 U.S.C. § 119 to Japanese Application No. 2010-282275, filed Dec. 17, 2010, the entire content of which is also incorporated herein by reference.

TECHNICAL FIELD

The present invention relates to a protective structure of a substance to be protected and its use, and a method for protecting the substance to be protected.

BACKGROUND ART

A substance to be protected, such as an enzyme, has been used and studied in a wide variety of areas including detergents, textile industry, glycation industry, pharmaceuticals, agricultural chemicals, brewing, cosmetic products and the like. However, a problem of the enzyme is that the enzyme readily induces deactivation. Thus, when treating the enzymes in the lab, they should be stored in the form of a powder or a concentrated aqueous solution at −20° C. or for long-term storage, stored at low temperature of −80° C. It is also necessary to determine their activity before use.

On the other hand, outside the laboratory (for example, at the distribution level or in the home), the enzymes are stored typically at ambient temperature and impossible to determine their activity. In order to effectively use the enzymes outside the laboratory, they need to be formed in the form of a less-scattering granule or in a liquid form usable when used so that they can be stored even at ambient temperature.

To allow the enzymes to be treated in a liquid state, using an emulsion can be considered. To inhibit enzymatic deactivation caused by surfactant used in the emulsion, in a conventional household detergent and the like, measures have been taken, such as the addition of an enzyme stabilizing agent, or adsorptive immobilization of the enzymes or encapsulation of them in a protective capsule (for example, Patent Document 1). However, even so, the enzymes allow enzyme activity thereof to be still decreased significantly when in use.

The enzyme material, a dye and the like which may involve the decreased function, such as color degradation, due to outside stimuli, such as light and the like, are in common in that they have to be protected from the outside stimuli while kept in a liquid state.

Patent Document 1: Japanese Translation of PCT International Publication, Publication No. 2009-532566

DISCLOSURE OF THE INVENTION

Problems to be Solved by the Invention

The present invention has been made in light of these circumstances, and an object thereof is to provide a structure and a method capable of protecting from outside stimuli while containing in a liquid state a water-dispersible substance to be protected.

Another object of the present invention is to provide a protective structure of the enzyme material, which is excellent in maintaining the enzyme activity while containing the enzyme material in a liquid state. Still another object of the present invention is to provide an enzymatic reaction method using such protective structure of the enzyme material, a method of producing reaction product, a method for adjusting the speed of enzymatic reaction, and an enzyme material use kit.

Means for Solving the Problems

The present inventors have found that an aqueous phase containing the substance to be protected, such as an enzyme material, is protected from the outside stimuli by dispersing the aqueous phase in an oil phase by means of either vesicles formed with an amphiphilic substance which spontaneously forms vesicles, or polycondensation polymer particles, and thereby, the present invention has been accomplished. Specifically, the present invention provides the followings:

(1) A protective structure of a substance to be protected having a water-in-oil emulsion structure comprising: an aqueous phase composing a discontinuous phase containing a water-dispersible substance to be protected; an oil phase in which the aqueous phase is dispersed; and vesicles formed with an amphiphilic substance which spontaneously forms vesicles, or polycondensation polymer particles having hydroxyl groups.

(2) The protective structure according to (1), wherein the substance to be protected contains one or more enzyme materials or dye.

(3) The protective structure according to (2), wherein the substance to be protected contains one or more enzyme materials, and
the protective structure contains the vesicles.

(4) The protective structure according to (3), wherein the enzyme material contained in one aqueous phase is different from the enzyme material contained in the other aqueous phase.

(5) The protective structure according to (4), wherein the enzyme material contained in one aqueous phase has the activity to inhibit the enzyme material contained in the other aqueous phase, if both of these enzyme materials are present in the same aqueous phase.

(6) A method for protecting from outside stimuli the substance to be protected, which comprises: dispersing the protective structure according to any one of (1) to (5) in the aqueous phase by means of either vesicles formed with the amphiphilic substance which spontaneously forms vesicles or polycondensation polymer particles having hydroxyl groups to form a water-in-oil-in-water emulsion.

(7) The method according to (6), wherein the outside stimuli are one or more selected from the group consisting of pH and salt concentration of the outer aqueous phase of the water-in-oil-in-water emulsion, a substance which is contained in the outer aqueous phase and causes either decomposition or decreased function of the substance to be protected, and light, an electric field, an electromagnetic wave and an acoustic wave which are applied to the outer aqueous phase.

(8) An enzymatic reaction method, which comprises the steps of:

dispersing the protective structure according to any one of (3) to (5) in the aqueous phase by means of the vesicles formed with the amphiphilic substance which spontaneously forms vesicles to form the water-in-oil-in-water emulsion; and applying a substrate contained in the outer aqueous phase to an enzymatic reaction caused by the enzyme material.

(9) A method for producing a reaction product, which comprises the steps of: dispersing the protective structure according to any one of (3) to (5) in the aqueous phase by means of the vesicles formed with the amphiphilic substance which spontaneously forms vesicles to form the water-in-oil-in-water emulsion; and applying the substrate contained in the outer aqueous phase to the enzymatic reaction caused by the enzyme material to produce a reaction product of the substrate.

(10) A method for adjusting the speed of the enzymatic reaction caused by the enzyme material by increasing or decreasing the amount of the oil phase to the amount of the aqueous phase in the protective structure according to any one of (3) to (5).

(11) An enzyme material use kit, containing: the protective structure according to any one of (3) to (5); and a vesicle solution containing the vesicles formed with the amphiphilic substance which spontaneously forms vesicles.

(12) The use kit according to (11), which is used as a detergent.

Effects of the Invention

According to the present invention, since an aqueous phase composing a discontinuous phase containing one or more substances to be protected is dispersed by means of either vesicles formed with an amphiphilic substance which spontaneously forms vesicles, or polycondensation polymer particles having hydroxyl groups, it is possible to protect from outside stimuli while containing in a liquid state the substance to be protected.

Also, since the aqueous phase composing a discontinuous phase containing one or more enzyme materials is surrounded with the vesicles formed with an amphiphilic substance which spontaneously forms vesicles and then dispersed, it is possible to maintain the enzyme activity while containing the enzyme material in a liquid state.

BRIEF DESCRIPTION OF THE DRAWINGS

FIG. 5 is a graph showing a change in enzyme activity of the protective structure of the enzyme material in FIG. 4.

FIG. 6 is a graph showing a change in enzyme activity of the protective structure of the enzyme material according to yet another Example of the present invention.

PREFERRED MODE FOR CARRYING OUT THE INVENTION

Figure 1:
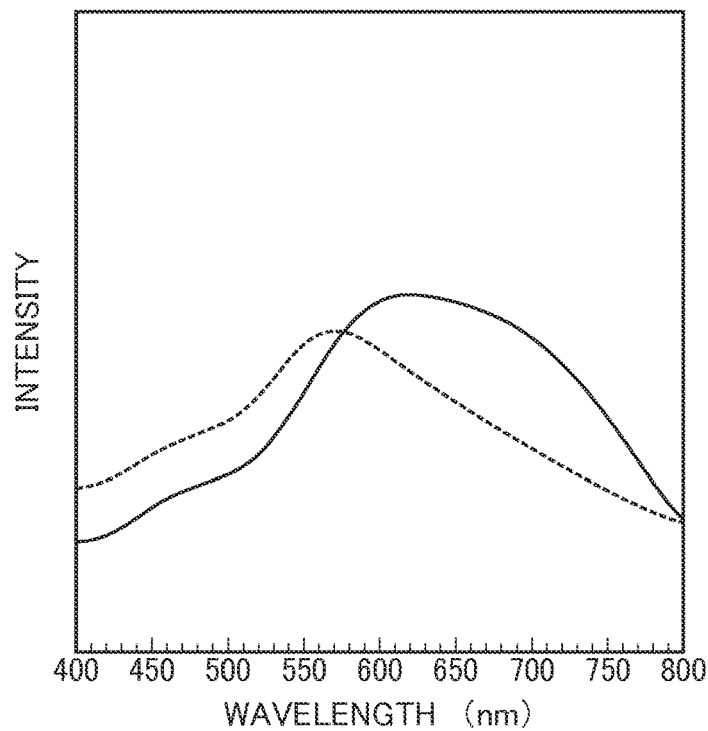
FIG. 1 is a graph showing enzyme activity in Comparative Example.

Embodiments of the present invention will be described below, but these embodiments are not intended to limit the scope of the present invention.

Protective Structure of Substance to be Protected

A protective structure of an enzyme material according to the present invention has a water-in-oil emulsion structure comprising: an aqueous phase composing a discontinuous phase containing a water-dispersible substance to be protected; an oil phase in which the aqueous phase is dispersed; and vesicles formed with an amphiphilic substance which spontaneously forms vesicles, or polycondensation polymer particles having hydroxyl groups. Such protective structure is protected from outside by the oil phase and also makes it possible to stably form a water-in-oil-in-water emulsion having an outer aqueous phase on the outermost side thereof, and even then, the oil phase also acts as a protective layer. Herein, emulsification by the vesicles or the polycondensation polymer particles is expected to be due to the interposition of the vesicles or the polycondensation polymer particles on the both interfaces between the aqueous phase and the oil phase.

The water-dispersible substance to be protected is not particularly limited as long as it is water soluble or hydrophilic and is to be protected from outside stimuli. Examples of the water-dispersible substance include an enzyme material, dye and a free-radical containing substance. The enzyme material may be protected from deactivation caused by the outside stimuli such as pH and salt concentration which are out of the optimal range, decomposition of the enzyme material, or a substance which causes decreased function, and the dye may be protected from color degradation and precipitation which are caused by the outside stimuli such as pH and salt concentration or light.

Examples of the dye include, but are not particularly limited to, oxidation-reduction dye such as methylene blue, new methylene blue, neutral red, indigocarmine, acid red, safranine T, phenosafranine, capri blue, nile blue, diphenylamine, xylene cyanol, nitrodiphenylamine, ferroin and N-phenylanthranilic acid.

For the protective structure of the enzyme material according to an embodiment, it is preferred to use the vesicles in that it is not metabolized by the enzyme materials. The vesicles formed with the amphiphilic substance which spontaneously forms vesicles, unlike surfactants, may not lead to the deactivation of the enzyme material, and the aqueous phase which contains the enzyme material may be protected from outside by the oil phase. This makes it possible to maintain the enzyme activity while containing the enzyme material in a liquid state.

The enzyme material contained in the aqueous phase may be alone or a plurality of enzyme materials. In the latter case, different types of the enzyme materials may be concurrently present in the same aqueous phase, or separately present in different aqueous phases. In the latter case, the enzyme material contained in one aqueous phase (referred to as a first enzyme material for convenience) differs from the enzyme material contained in the other aqueous phase (referred to as a second enzyme material for convenience), and thus making it possible to inhibit the first enzyme material and the second enzyme material from acting on each other. This is especially useful when the first enzyme material (for example, a proteolytic enzyme) may have an activity to inhibit the second enzyme material if they are present together in the same aqueous phase. This may concurrently induce the enzyme activity of both of the first enzyme material and the second enzyme material in the same system without any inhibition.

The enzyme materials may be appropriately selected from anything depending on its use. For example, when using the protective structure of the enzyme material as a detergent, the enzyme material may be a degrading enzyme such as a proteolytic enzyme, glycolytic enzyme or the like, and when using the protective structure of the enzyme material for synthesis, the enzyme material may be a synthesis enzyme.

As well as the enzymes, the aqueous phase may also contain an optional component. Examples of the optional component include an enzyme stabilizing agent (for example, boron compound, calcium ion source, bihydroxy compound, formic acid).

Examples of the amphiphilic substance include, but are not particularly limited to, derivatives of polyoxyethylene hydrogenated castor oil of the following general formula 1, or halide salt derivatives of di-alkyl ammonium derivatives, tri-alkyl ammonium derivatives, tetra-alkyl ammonium derivatives, di-alkenyl ammonium derivatives, tri-alkenyl ammonium derivatives or tetra-alkenyl ammonium derivatives of the general formula 2.

General Formula 1:

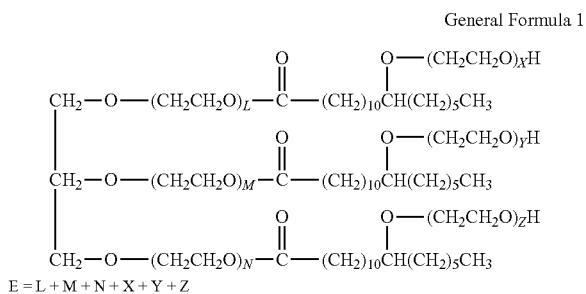

wherein E as an average number of moles of added ethylene oxide may be from 3 to 100, but is not particularly limited.

General Formula 2:

wherein $R_1$ and $R_2$ each independently represent an alkyl group or alkenyl group having 8 to 22 carbon atoms; $R_3$ and $R_4$ each independently represents hydrogen or an alkyl group having 1 to 4 carbon atoms; and X is F, Cl, Br or I.

As the amphiphilic substance, phosphatide and derivatives thereof may be employed. It is possible to employ, as the phosphatide, 1,2-dilauroyl-sn-glycero-3-phospho-rac-1-choline (DLPC) having a chain length of 12 carbon atoms, 1,2-dimyristoyl-sn-glycero-3-phospho-rac-1-choline (DMPC) having a chain length of 14 carbon atoms, and 1,2-dipalmitoyl-sn-glycero-3-phospho-rac-1-choline (DPPC) having a chain length of 16 carbon atoms, among constituents of the following general formula 3.

General Formula 3:

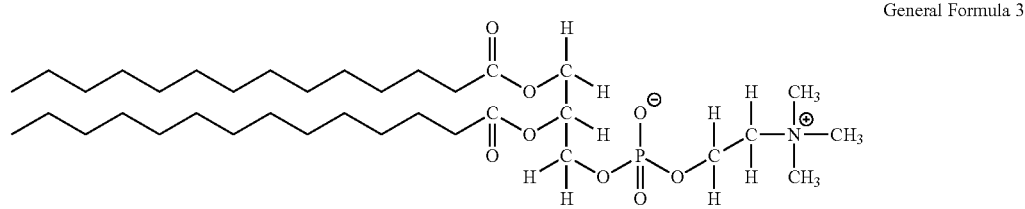

It is possible to employ Na salt or NH₄ salt of 1,2-dilauroyl-sn-glycero-3-phospho-rac-1-glycerol (DLPG) having a chain length of 12 carbon atoms, Na salt or NH₄ salt of 1,2-dimyristoyl-sn-glycero-3-phospho-rac-1-glycerol (DMPG) having a chain length of 14 carbon atoms, Na salt or NH₄ salt of 1,2-Dipalmitoyl-sn-glycero-3-phospho-rac-1-glycerol (DPPG) having a chain length of 16 carbon atoms, among constituents of the following general formula 4.

General Formula 4:

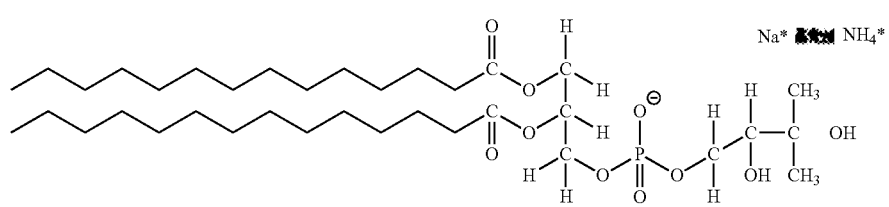
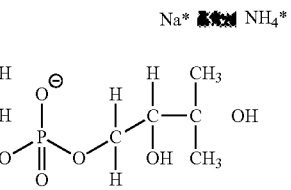

General Formula 4

Further, as the phosphatide, egg-yolk lecithin or soy lecithin or the like may be employed.

Furthermore, polyglyceryl fatty acid esters of General Formula 5 may be used. Examples of the polyglyceryl fatty acid esters include, but are not limited to, esters of a fatty acid having 12 to 36 carbon atoms with a polyglycerol having a degree of polymerization of 6 or more, particularly of 6 to 10. The fatty acid which forms esters by reacting with polyglycerol may be any fatty acids of a saturated, unsaturated, linear or branched fatty acid, and specific examples thereof include capric acid, lauric acid, isotridecanoic acid, myristic acid, palmitic acid, palmitoleic acid, stearic acid, isostearic acid, oleic acid, linoleic acid, behenic acid and recinoleic acid.

General Formula 5:

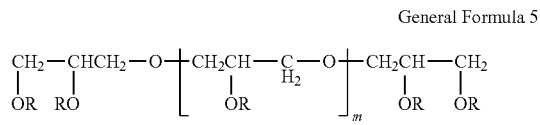

General Formula 5 wherein R represents H, or a saturated or unsaturated fatty acid.

The vesicles formed with the amphiphilic substance can be produced by adding the above amphiphilic substance to the dispersion media (which is the oil phase in this embodiment), followed by stirring. Such vesicles have an average particle size within a range from 200 nm to 800 nm before the formation of the emulsion, and have an average particle size within a range from 8 to 500 nm within the water-in-oil emulsion structure.

The polycondensation polymer having hydroxyl groups may be either a natural polymer or a synthetic polymer and be appropriately selected depending on the use of the emulsifier. However, the natural polymer is preferable in terms of its excellent stability and typically low cost, and in terms of excellent capability of emulsification, the following polysaccharide is more preferable.

The polysaccharide is a polymer having a glucoside structure, such as cellulose or starch. Examples thereof include those from which microorganisms produce, as component, some saccharides of monosaccharides, such as ribose, xylose, rhamnose, fucose, glucose, mannose, glu-curonic acid and gluconic acid; natural polymers such as xanthan gum, gum arabic, guar gum, karaya gum, carrageenan, pectin, fucoidan, quinseed gum, trant gum, locust bean gum, galactomannan, curdlan, gellan gum, Fucogel, casein, gelatin, starch, collagen and the like; a semisynthetic polymer, such as methyl cellulose, ethyl cellulose, methylhydroxypropylcellulose, carboxymethyl cellulose, hydroxymethyl cellulose, hydroxypropyl cellulose, sodium carboxymethyl cellulose, propylene glycol alginate, cellulose crystal, starch-sodium acrylate graft polymer, hydrophobized hydroxypropyl methylcellulose and the like; the synthetic polymer, such as polyvinyl alcohol, polyvinyl pyrrolidone, carboxyvinyl polymer, polyacrylate and polyethylene oxide.

Dispersion may be conducted according to a conventional method depending on the polycondensation polymer used. For example, for starch, dispersing it sufficiently in water at room temperature, and for xanthan gum, generally adding to hot water.

The vesicles formed with an amphiphilic substance and polycondensation polymer particles allow a wide variety of combinations of the aqueous phase and the oil phase to be emulsified (for details, see Japanese Patent No. 3855203). Therefore, the oil phase may not be particularly limited and be any oils such as light oil, Bunker A, Bunker C, tar, biodiesel fuel, reclaimed heavy oil, waste edible oil, oil solution derived from natural product (vegetable oil, mineral oil), and among them, from the viewpoint of the fact that it is hard to inhibit the enzyme activity, a nonpolar oil such as liquid paraffin or squalane is preferred.

A ratio between the aqueous phase and the oil phase may be set within an acceptable range depending on solubility of the enzyme material, the final necessary amount of the enzyme material, capability of emulsification of the vesicles formed with the amphiphilic substance, or the polycondensation polymer particles and the like, and it may be set typically in a ratio of the aqueous phase to the oil phase of from 5:95 to 50:50 (mass ratio). Herein, with increasing the ratio of the oil phase, the oil phase in the water-in-oil emulsion particles dispersed in the water-in-oil-in-water emulsion described below increases in thickness to for example, result in a decrease in the reaction rate of the enzyme, while with decreasing the ratio of the oil phase, the oil phase in the water-in-oil emulsion particles dispersed in the water-in-oil-in-water emulsion decreases in thickness to for example, result in an increase in the reaction rate of the enzyme. Thus, for example, the ratio between the aqueous phase and the oil phase may be set appropriately depending on the required reaction rate of the enzyme.

The inner aqueous phase in the water-in-oil-in-water emulsion should be had at least one water droplet.

The protective structure of the substance to be protected such as the enzyme material may be produced by, for example, adding the amphiphilic substance or the polycondensation polymer and stirring them to prepare a dispersion, and adding the substance to be protected to the dispersion in a predetermined ratio, followed by stirring with the oil solution. Detailed procedures may be performed in accordance with a conventionally known method (for example, Japanese Patent No. 3855203).

Method for Protecting Substance to be Protected

The present invention further includes a method for protecting from outside stimuli the substance to be protected, the method comprising: dispersing the aforementioned protective structure in the aqueous phase by means of either vesicles formed with the amphiphilic substance which spontaneously forms vesicles, or polycondensation polymer particles having hydroxyl groups to form a water-in-oil-in-water emulsion.

The outside stimuli may, but not be particularly limited thereto, be one or more selected from the group consisting of pH and salt concentration of the outer aqueous phase of the water-in-oil-in-water emulsion, a substance which is contained in the outer aqueous phase and causes decomposition or decreased function of the substance to be protected, and light, an electric field, an electromagnetic wave and an acoustic wave (especially, ultrasonic waves) which are applied to the outer aqueous phase.

The substance to be protected, the amphiphilic substance and the polycondensation polymer are the same as mentioned above and therefore, will not be illustrated further.

Enzyme Material Use Kit

The enzyme material use kit according to the present invention contains: the aforementioned protective structure; and a vesicle solution containing the vesicles formed with the amphiphilic substance which spontaneously forms vesicles. The vesicle solution is dispersed water in which the vesicles are dispersed in water, and by mixing the protective structure and the vesicle solution, a water-in-oil-in-water emulsion may be formed. By containing a substrate of the enzyme material in the outermost aqueous phase (or the outer aqueous phase) in the water-in-oil-in-water emulsion, the enzymatic reaction may be developed while inhibiting enzymatic deactivation.

Within the use kit, the protective structure and the vesicle solution may be concurrently present in the same system or separately stored individually. Since the former meets conditions under which the enzymatic reaction may be developed, it has an advantage in that it is ready-to-use, and in this case, the protective structure and the vesicle solution may be either in a state of a water-in-oil-in-water emulsion or in the previous state thereto. Because the latter does not meet the appropriate condition to develop the enzymatic reaction, it provides more excellent storage stability of the enzyme.

The vesicle solution may also contain an optional component, as well as the vesicles formed with the amphiphilic substance. Examples of the optional component include a substance involved in the enzymatic reaction, such as a substrate or an enzyme stabilizing agent (for example, boron compound, calcium ion source, a bihydroxy compound or formic acid).

Such use kit mixes the protective structure and the vesicle solution (if needed, water may be added therein) to form the water-in-oil-in-water emulsion, and if placed under the condition of the enzymatic reaction, applies the substrate contained in the outer aqueous phase to the enzymatic reaction caused by the enzyme material. Since the vesicles, unlike a surfactant, may not induce deactivation of the enzyme material, the aqueous phase containing the enzyme material may be protected from outside by the oil phase. Thus, it is possible to maintain the enzyme activity while containing the enzyme material in a liquid state.

Since the use kit of the present invention is able to maintain the enzyme activity while containing the enzyme material in a liquid state, it is available for a variety of uses. The uses may, but not be particularly limited thereto, be washing clothes or the like, chemical synthesis, study of the enzyme material, and the like. As mentioned above, the protective structure of the present invention allows even the enzyme materials which have the activity to inhibit each other when present together in the same aqueous phase to cause the enzyme activity without any inhibition from each other by separately containing the enzyme materials in different aqueous phases. This may sufficiently induce the enzyme activity and also cause more than one enzymatic reaction concurrently.

Further, the present invention provides an enzymatic reaction method, which comprises the steps of: dispersing the protective structure in the aqueous phase by means of the vesicles formed with the amphiphilic substance which spontaneously forms vesicles to form the water-in-oil-in-water emulsion; and applying the substrate contained in the outer aqueous phase to the enzymatic reaction caused by the enzyme material.

Furthermore, the present invention provides a method for producing a reaction product, which comprises the steps of: dispersing the protective structure in an aqueous phase by means of the vesicles formed with an amphiphilic substance which spontaneously forms vesicles to form the water-in-oil-in-water emulsion; and applying the substrate contained in the outer aqueous phase to the enzymatic reaction caused by the enzyme material to produce a reaction product of the substrate. For example, a use in combination with the enzyme involved in each of multiple steps of synthesis may provide a consistent production from a starting material to a final product without treating intermediate products. The resulting products may be removed to the outer aqueous phase by demulsifying the emulsion.

The present invention also provides a method for adjusting the speed of the enzymatic reaction caused by the enzyme material, by increasing or decreasing the amount of the oil phase to the amount of the aqueous phase in the protective structure. As mentioned above, the enzymatic reaction caused by the enzyme material has been understood to be inversely proportionate to the thickness of the oil phase in the water-in-oil emulsion, and therefore, the thickness of the oil phase may be adjusted by increasing or decreasing the amount of the oil phase to the amount of the aqueous phase to adjust the speed of the enzymatic reaction.

EXAMPLES

α-Amylase

Comparative Example 1

α-Amylase "SDH6665" (manufactured by Wako Pure Chemical Industries, Ltd.) was dissolved in ion-exchanged water to be 0.01% by mass, and then 3 mL of 0.1% by mass of amylose "EC2326859" (manufactured by Wako Pure Chemical Industries, Ltd.) and an appropriate amount of citric acid were added to 100 μL of the resulting aqueous enzyme solution, followed by maintaining at 37° C. for 5 minutes. Then, a hydrochloric acid solution as quenching agent was added to quench the reaction before centrifuged (5,000 rpm, 2 minutes), and then the reaction solution was extracted. To each of the reaction solution and the solution before the reaction, a drop of 0.1% by mass aqueous solution of iodide was added, and then the spectrum was measured using an ultraviolet-visible spectrophotometer "V-570" (manufactured by JASCO Corporation) (FIG. 1). As shown in FIG. 1, it was found that the maximal absorption wavelength after the reaction (dashed line) was shifted to 570 nm, in contrast to the maximal absorption wavelength before the reaction (solid line) of 621 nm, and that α-amylase had the enzyme activity. Also, since the enzyme in itself, as is well known, is to be deactivated drastically in a normal state, the enzymatic reaction was conducted in the environment capable of sufficient inhibition of deactivation.

Example 1

HCO-10 was added to water to be the concentration of 5% by mass, followed by maintaining at 20±5° C. and further stirring using DESKTOP QUICK HOMOMIXER "LR-19" (manufactured by MIZUHO Industrial CO., LTD.) at 1,300±100 rpm for 30 minutes to prepare a dispersion of the vesicles formed with the amphiphilic substance. To liquid paraffin, HCO-5 was added to be 0.1% by mass, followed by stirring using a magnetic stirrer for 30 minutes. To the resulting dispersion, the aqueous enzyme solution used in Comparative Example 1 was added to be a mass ratio of the aqueous enzyme solution to the dispersion of 10:90, followed by stirring using a homomixer "Heidolph DIAX900" at 16,000 rpm for 5 minutes to prepare a water-in-oil emulsion as a protective structure of an enzyme material. This emulsion was added to the dispersion of HCO-10 in water to be a mass ratio of the emulsion to the dispersion of 50:50, followed by stirring using the homomixer at 16,000 rpm for 5 minutes to prepare a water-in-oil-in-water composite emulsion containing the enzyme.

Figure 2:
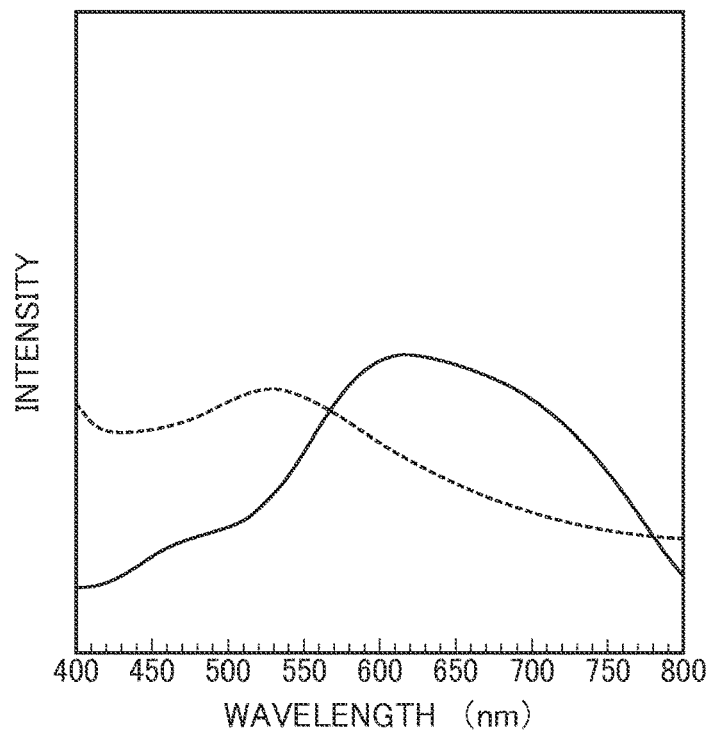
FIG. 2 is a graph showing enzyme activity of the protective structure of the enzyme material according to one Example of the present invention.

By the same procedure as in Comparative Example 1, except that 100 μL of the water-in-oil-in-water emulsion was added, the spectrum was measured (FIG. 2). As shown in FIG. 2, it was found that the maximal absorption wavelength after the reaction (dashed line) was shifted to 526 nm, in contrast to the maximal absorption wavelength before the reaction (solid line) of 621 nm, and that α-amylase had the enzyme activity even in the water-in-oil-in-water emulsion.

Figure 3:
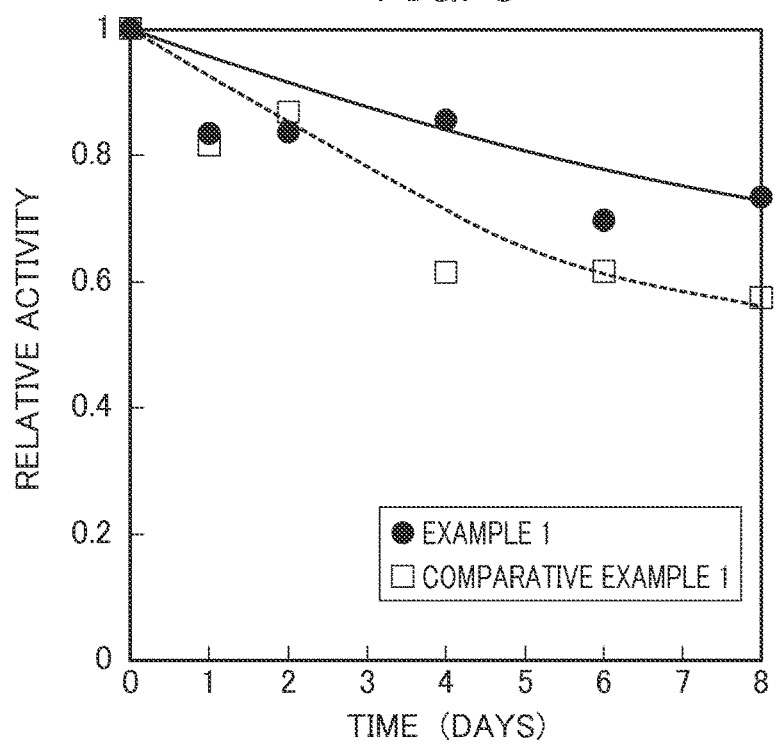
FIG. 3 is a graph showing a change in enzyme activity of the protective structure of the enzyme material in FIG. 2.

The solutions before addition of the substrates in Comparative Example 1 and Example 1 were stored at 4° C. and subjected to the measurement of the enzyme activity every day for 1 week (FIG. 3). As shown in FIG. 3, it was found that Example 1 inhibited the enzymatic deactivation over Comparative Example 1.

Papain

Comparative Example 2

Papain "WKP5559" (manufactured by Wako Pure Chemical Industries, Ltd.) was dissolved in ion-exchanged water to be 2.0% by mass to be a solution, and into 0.1 mL of the solution, 1 mL of 1.0% by mass of casein "LTQ4396" (manufactured by Wako Pure Chemical Industries, Ltd.) and an appropriate amount of phosphate buffer were added, followed by maintaining at 37° C. for 5 minutes. Thereafter, a quenching agent trichloroacetic acid solution was added to quench the reaction before filtered to obtain a filtrate, and then an amount of the reaction product phenylalanine was measured using ultraviolet-visible spectrophotometer "V-570" (manufactured by JASCO Corporation) (FIG. 4).

Example 2

By the same procedure as in Example 1, except that the aqueous enzyme solution used in Comparative Example 2 was used, the water-in-oil-in-water composite emulsion was prepared. By the same procedure as in Comparative Example 2, except that this emulsion was used, the amount of phenylalanine was determined (FIG. 4).

Figure 4:
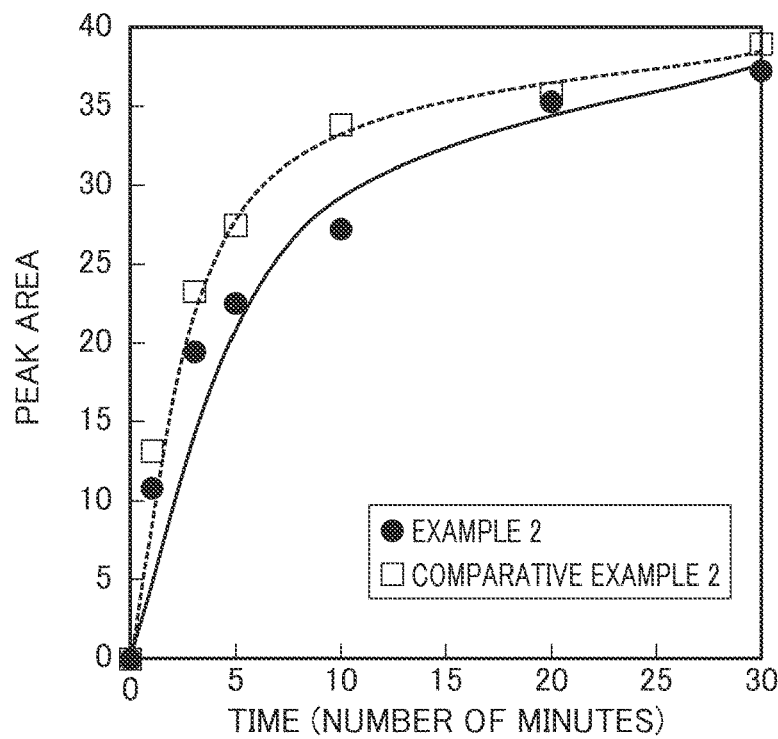
FIG. 4 is a graph showing enzyme activity of the protective structure of the enzyme material according to another Example of the present invention.

As shown in FIG. 4, an initial speed of the reaction in Example 2 was slightly slower than the one in Comparative Example 2, but the difference between them was reduced with time to be equal to each other after 30 minutes. This showed that the comparable enzyme activity was also obtained in the water-in-oil-in-water emulsion.

In Comparative Example 2 and Example 2, each of the solutions before adding the substrate was stored at 4° C., and then the enzyme activity was measured over 2 weeks (FIG. 5). FIG. 5 showed that Papain, which was a proteolytic enzyme and extremely hard to be deactivated, inhibited the deactivation in Example 2 in the same manner as in Comparative Example 2.

α-Amylase and Papain

Comparative Example 3

The aqueous enzyme solutions prepared in Comparative Example 1 and Comparative Example 2 were added in a ratio of 50:50 (mass ratio), followed by stirring to mix them together.

Example 3

The water-in-oil-in-water emulsion prepared in Example 1 and Example 2 were added in a ratio 50:50 (mass ratio), followed by stirring for 3 minutes to mix them together.

The mixtures in Comparative Example 3 and Example 3 were subjected to the measurement of papain enzyme activity over 2 weeks (FIG. 6). FIG. 6 shows that papain, even when mixed with α-amylase, almost never leads to deactivation in the same way as papain alone (FIG. 5), and that even after 14 days, maintains the high activity both in the emulsion and the aqueous solution. This showed that the proteolytic enzyme papain made it possible to maintain the enzyme activity without any inhibition by the amylolytic enzyme α-amylase.

Figure 7:
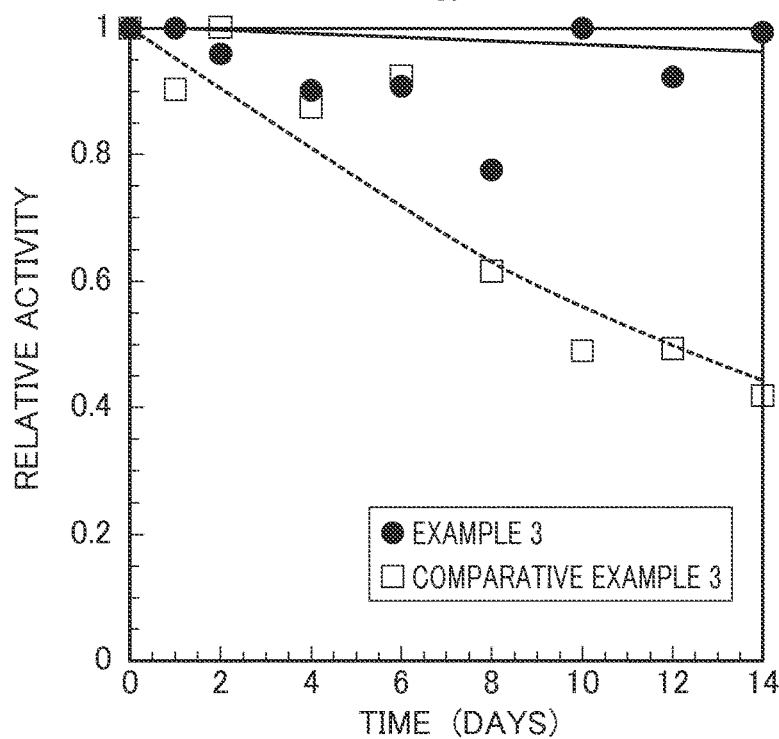
FIG. 7 is a graph showing a change in another enzyme activity of the protective structure of the enzyme material in FIG. 6.

Also, the mixtures in Comparative Example 3 and Example 3 were subjected to the measurement of the α-amylase enzyme activity over 2 weeks under the above conditions (FIG. 7). While α-amylase in an emulsion state was almost never deactivated, the α-amylase enzyme activity in one-liquid component system in the form of solution was drastically reduced days later. The reduced rate is clearly increased compared to the one in the absence of papain (FIG. 3). While the results of Comparative Example 3 was considered to be resulted from the decomposition of α-amylase caused by the proteolytic enzyme papain, it was found in Example 3 to inhibit the deactivation in the same way as in the absence of papain (FIG. 3) and to protect α-amylase from papain.

Figure 8:
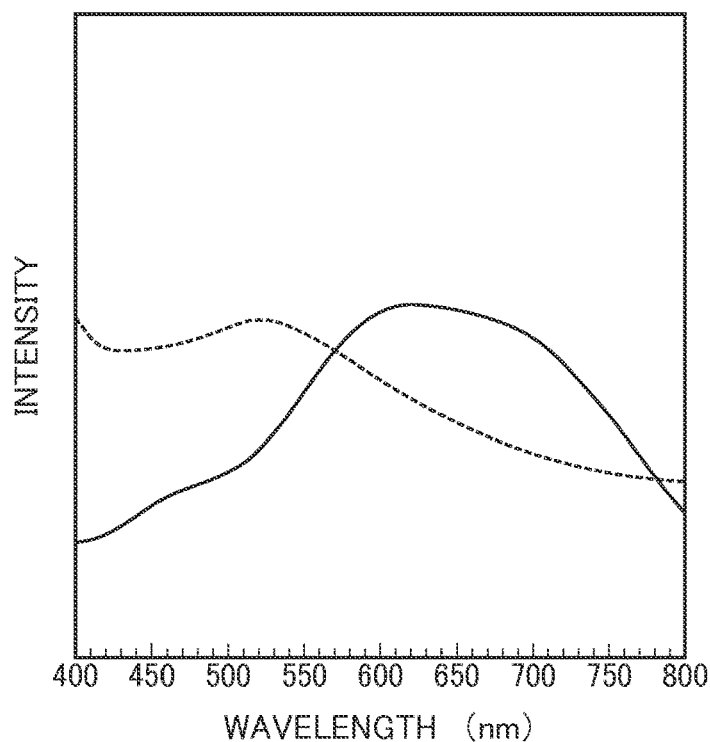
FIG. 8 is a graph showing enzyme activity of the protective structure of the enzyme material in FIG. 6.

Next, except that both of casein and amylose were concurrently added to the mixture of Example 3, the enzyme activity was determined under the above conditions. FIG. 8 shows ultraviolet absorbing spectra (representing α-amylase enzyme activity) measured after the liquids between before and after the reaction are applied to the iodine reaction, and FIG. 9 shows a graph of papain enzyme activity based on the amount of phenylalanine.

As shown in FIG. 8, the maximal absorption wavelength was shifted from 623 nm yielded before the reaction (solid line) to 521 nm yielded after the reaction (dashed line), which was the same result as the one yielded in the presence of the substrate alone (FIG. 2). This showed that even when the one-component emulsion was reacted with the solution containing the substrate, α-amylase was reacted with amylose due to the specificity of substrate to develop the enzymatic decomposition reaction.

Figure 9:
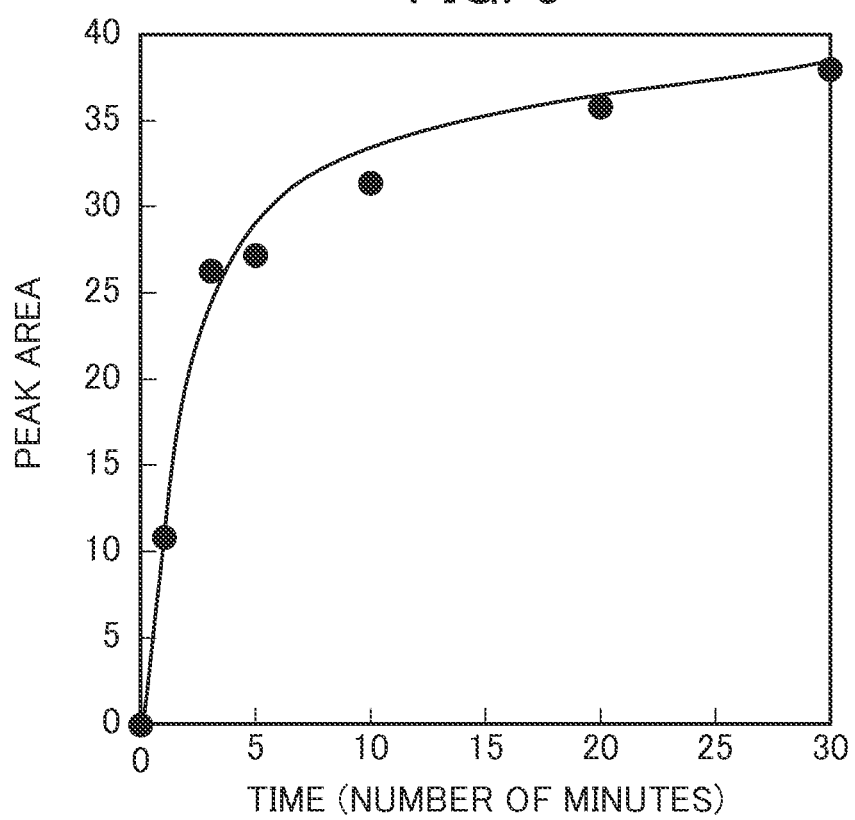
FIG. 9 is a graph showing another enzyme activity of the protective structure of the enzyme material as shown in FIG. 6.

The enzyme activity of papain shown in FIG. 9 was the same result as the one yielded in the presence of the substrate alone (FIG. 4). This showed that even when the one-component emulsion was reacted with the solution containing the substrate, papain was reacted with casein due to the specificity of substrate to develop the enzymatic decomposition reaction.

Ratio Between Aqueous Phase and Oil Phase

Example 4

By the same procedure as in Example 1, except that the use of the aqueous enzyme solution obtained by dissolving alkaline phosphatase "EC3.1.3.1" (manufactured by Wako Pure Chemical Industries, Ltd.) in ion-exchanged water to be 0.1% by mass, a water-in-oil-in-water composite emulsion containing enzyme was prepared. However, an additive ratio of the dispersion of liquid paraffin used for forming the water-in-oil emulsion was to be 70, 75, 80, 85, 90% by mass based on a total mass of the dispersion and the aqueous enzyme solution.

Figure 10:
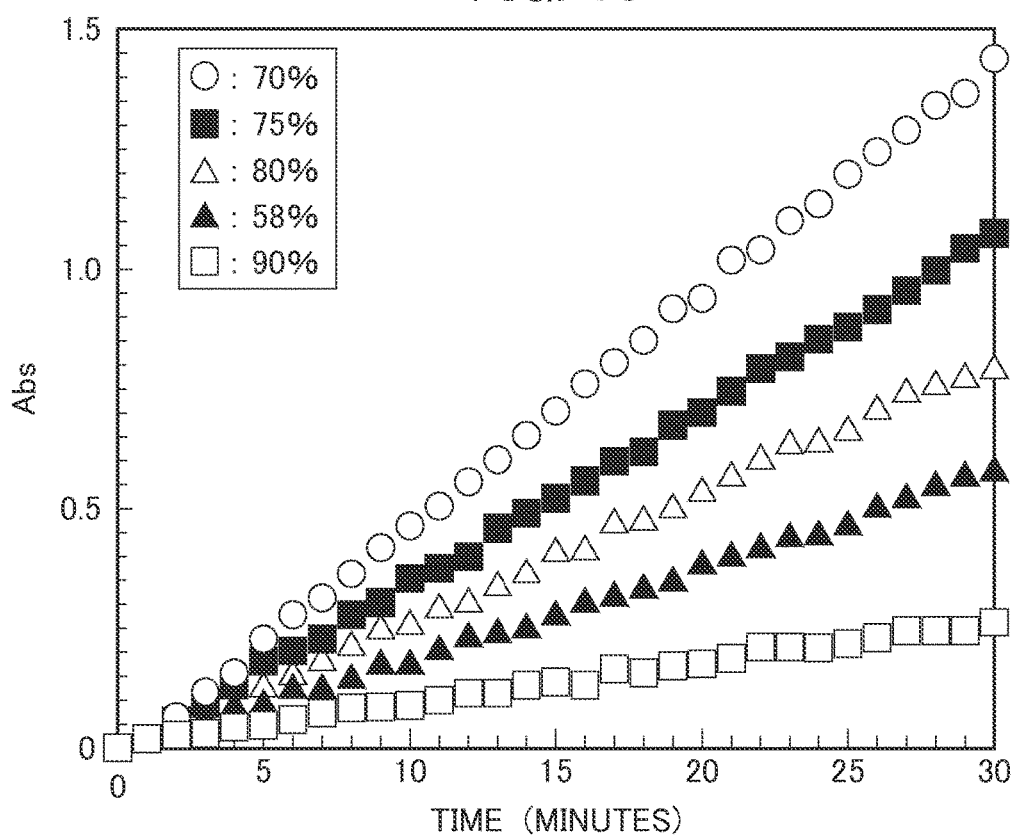
FIG. 10 is a graph showing a change in enzyme activity of the protective structure of the enzyme material according to still yet another Example of the present invention.

Each of the water-in-oil-in-water emulsions, resulted by using disodium p-nitrophenyl phosphate as a substrate, was subjected to the measurement of absorbance at wavelength of 410 nm using an ultraviolet-visible spectrophotometer "V-570" (manufactured by JASCO Corporation) according to the conventional method (FIG. 10). As shown in FIG. 10, the speed of the enzymatic reaction was inversely proportionate to the amount of the oil phase added when preparing the water-in-oil emulsion. This showed that it was possible to adjust the speed of the enzymatic reaction caused by the enzyme material by increasing or decreasing the amount of the oil phase to the amount of the aqueous phase in the protective structure.

Dye

Example 5

By the same procedure as in Example 1, except that instead of HCO-10, polyglyceryl oleate ester was used to stabilizing the inner aqueous phase and polyglyceryl distearate ester was used to stabilizing the water-in-oil emulsion to the outer aqueous phase, and instead of the aqueous enzyme solution, an aqueous methylene blue solution (aqueous solution to water-in-oil emulsion=1:1) was used, a water-in-oil-in-water composite emulsion was prepared. The aqueous methylene blue solution, which is a colored solution having absorption maximum at wavelength of 660 nm, has been known to allow the chromophore to be photodegraded by the irradiation with visible light to result in color degradation of the solution.

As Comparative Example, an attempt to form the water-in-oil-in-water emulsion using the conventional surfactant known in the art instead of polyglyceryl fatty acid ester resulted in failure to produce the stable emulsion. Therefore, as Comparative Example, the aqueous methylene blue solution used in Example 5 was used.

Figure 11:
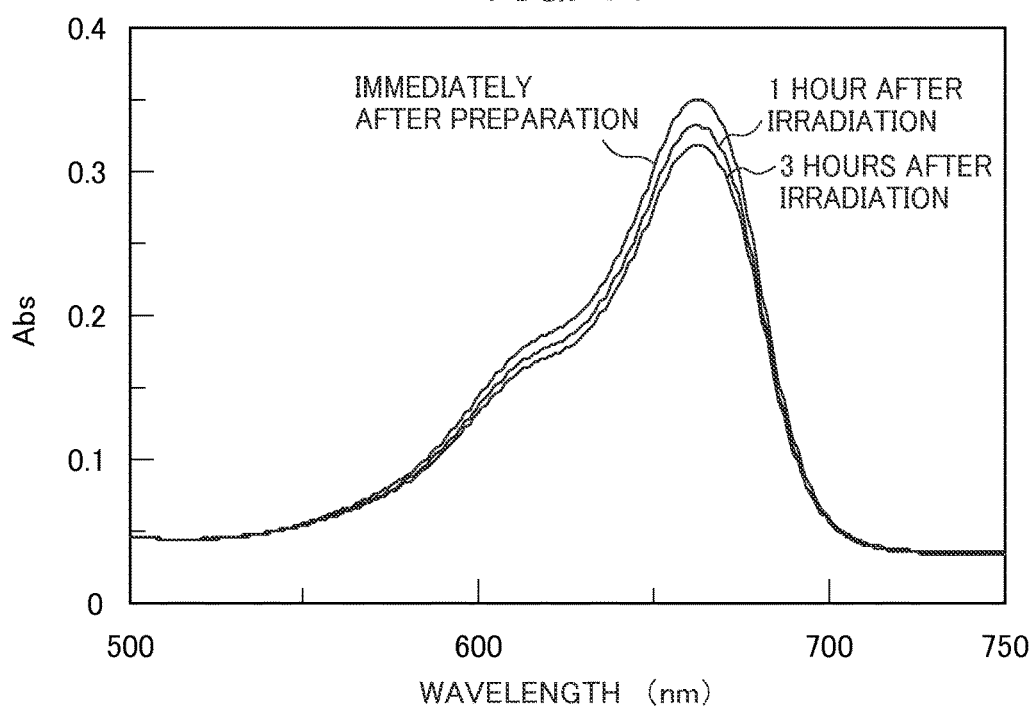
FIG. 11 is UV-VIS spectra showing color degradation with time of aqueous dye solutions according to Comparative Example.
Figure 12:
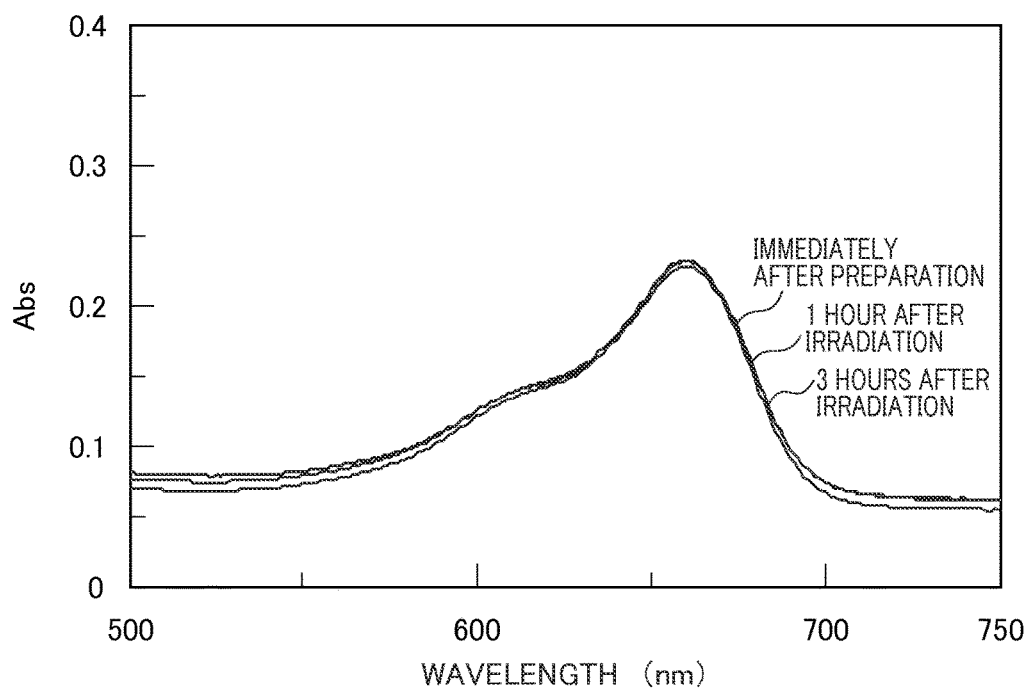
FIG. 12 is UV-VIS spectra showing color degradation with time of aqueous dye solution in the inner aqueous phase of the protective structure of the dye according to yet another Example of the present invention.

Each of the water-in-oil-in-water emulsion and the aqueous methylene blue solution in Comparative Example was irradiated with white light at an illumination intensity of 44.30 W/m$^2$ using an irradiation equipment "Luminal Ace LA-180Me" (manufactured by HAYASHI; 180W). Immediately after irradiation, 1 hour after irradiation and 3 hours after irradiation, UV-VIS spectra of the aqueous phase in the water-in-oil-in-water emulsion and the aqueous methylene blue solution as Comparative Example were obtained. The results are shown in FIGS. 11 (Comparative Example) and 12 (Example 5), respectively.

With increasing the irradiation time, while color degradation proceeded in Comparative Example, it was almost impossible to find the color degradation in Example 5. This showed that the water-in-oil-in-water emulsion of the present invention was able to provide a protection from the outside stimuli, such as light irradiation, with the substance to be protected. While it is obvious that Example 5 in which the inner aqueous phase is surrounded with the oil phase and the outer aqueous phase provides lower optical transmittance than Comparative Example, it should be noted that such stable water-in-oil-in-water emulsion has been ever difficult to be prepared by the conventional technology, and also that color degradation at 3 hours after irradiation in Example 5 is reduced when compared to the one at 1 hour after irradiation in Comparative Example.

Diffusional Inhibition

By the same procedure as in Example 1, except that an aqueous sodium hydroxide solution (pH 10.3) was used as the inner aqueous phase; pure water (pH 8.0) was used as the outer aqueous phase; a ratio of the outer aqueous phase to the inner aqueous phase was to be 2.0; medium chain triglyceryl was used instead of liquid paraffin as the oil phase; and decaglycerol distearate was used instead of HCO-10, a water-in-oil-in-water emulsion was prepared.

Figure 13:
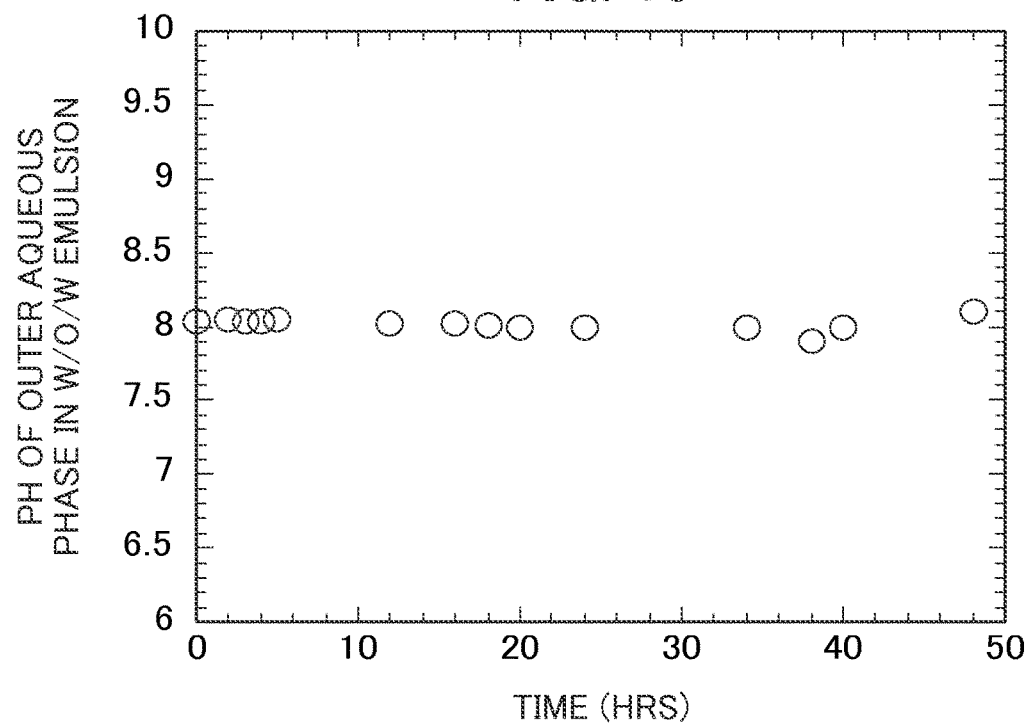
FIG. 13 is a graph showing a time-change in pH of the outer aqueous phase in the water-in-oil-in-water emulsion according to the Reference Example of the present invention.

The time-dependent measurements of pH of the outer aqueous phase after preparation are illustrated in FIG. 13. If diffusion occurred without any inhibition, the inner aqueous phase and the outer aqueous phase (in a ratio of 1:2) were to be homogeneously mixed to be pH of the outer aqueous phase of 9.04, but in fact, pH was kept constant at about 8.0. This showed that it was possible to inhibit the diffusion between the inner aqueous phase and the outer aqueous phase to protect the substance to be protected in the inner aqueous phase from outside stimuli such as pH, salt concentration and the like.

The invention claimed is:

1. A method of protecting a water-dispersible substance from outside stimuli and slowing decomposition or deactivation of the water-dispersible substance, the method comprising:

forming a protective structure having a water-in-oil emulsion structure surrounding the water-dispersible substance, wherein the protective structure comprises,
(a) (i) a first vesicle surrounding a first aqueous phase comprising the substance, wherein the first vesicle consists of a first amphiphilic substance which spontaneously forms vesicles, wherein the first vesicle has an average particle size of 8 to 500 nm, or
(a) (ii) first polycondensation polymer particles having hydroxyl groups and encapsulating the first aqueous phase;
and
(b) an oil phase being a different substance from the first vesicle and the first polycondensation polymer particles, wherein the first aqueous phase is dispersed in the oil phase as a discontinuous phase, wherein the first aqueous phase is dispersed in the oil phase while the first vesicle or the first polycondensation polymer particles encapsulate the first aqueous phase, and wherein the first vesicles or the first polycondensation polymer particles intervene on the boundary region between the first aqueous phase and the oil phase, forming a second vesicle encapsulating the protective structure or second polycondensation polymer particles encapsulating the protective structure, wherein the second vesicle is formed of a second amphiphilic substance which spontaneously forms vesicles, and wherein the second polycondensation polymer particles have hydroxyl groups; and dispersing the protective structure as a discontinuous phase in a second aqueous phase to form a water-in-oil-in-water emulsion, wherein the protective structure is dispersed in the second aqueous phase while the second vesicles or the second polycondensation polymer particles encapsulate the protective structure, wherein the second vesicle or the second polycondensation polymer particles intervene on the boundary region between the oil phase and the second aqueous phase, and wherein, the protective structure comprises:
(a) the first polycondensation polymer particles and the second polycondensation polymer particles;
(b) the first vesicle and the second vesicle;
(c) the first polycondensation polymer particles and the second vesicle, or
(d) the first vesicle and the second polycondensation particles,
wherein,
when the protective structure comprises (a) the first polycondensation polymer particles and the second polycondensation polymer particles or (c) the first polycondensation polymer particles and the second vesicle, only the first polycondensation polymer particles intervene on the boundary region between the first aqueous phase and the oil phase,
when the protective structure comprises (d) the first vesicle and the second polycondensation particles, only the first vesicle intervenes on the boundary region between the first aqueous phase and the oil phase.

2. The method according to claim 1, wherein the outside stimuli are selected from the group consisting of pH of the outer second aqueous phase of the water-in-oil-in-water emulsion, salt concentration of the outer second aqueous phase of the water-in-oil-in-water emulsion, a substance which is contained in the second aqueous phase and causes either decomposition or decreased function of the water-dispersible substance, light, an electric field, an electromagnetic wave applied to the second aqueous phase, and an acoustic wave applied to the second aqueous phase.

3. The method according to claim 1, wherein the water-dispersible substance comprises one or more enzymes or dyes.

4. The method according to claim 3, wherein the first aqueous phase is composed of two or more aqueous sub-phases surrounded by the first vesicle or the first polycondensation polymer particles; the water-dispersible substance is composed of two or more enzymes; a first enzyme contained in a first aqueous sub-phase is different from a second enzyme contained in a second aqueous sub-phase; the protective structure is composed of two or more protective structures; and a first protective structure contains the first aqueous sub-phase and a second protective structure contains the second aqueous sub-phase.

5. The method according to claim 4, wherein the first enzyme contained in the first aqueous sub-phase has an activity to inhibit the second enzyme contained in the second aqueous sub-phase.

6. An enzymatic reaction method comprising:
forming a protective structure having water-in-oil emulsion structure surrounding an enzyme, wherein the protective structure comprises
(a) (i) a first vesicle surrounding a first aqueous phase comprising the enzyme, wherein the first vesicle consists of a first amphiphilic substance which spontaneously forms vesicles, and the first vesicles has an average particle size of 8 to 500 nm, or
(a) (ii) first polycondensation polymer particles having hydroxyl groups encapsulating a first aqueous phase comprising the enzyme;
and
(b) an oil phase being a different substance from the first vesicle and the first polycondensation polymer particles, wherein the first aqueous phase is dispersed in the oil phase as a discontinuous phase, wherein the first aqueous phase is dispersed in the oil phase while the first vesicle or the first polycondensation polymer particles encapsulate the first aqueous phase, wherein the first vesicle or the first polycondensation polymer particles intervene on the boundary region between the first aqueous phase and the oil phase;

forming a second vesicle encapsulating the protective structure or second polycondensation polymer particles encapsulating the protective structure, wherein the second vesicle is formed of a second amphiphilic substance which spontaneously forms vesicles, wherein the second polycondensation polymer particles have hydroxyl groups;

dispersing the protective structure as a discontinuous phase in a second aqueous phase to form a water-in-oil-in-water emulsion, wherein the protective structure is dispersed in the second aqueous phase while the second vesicle or the second polycondensation polymer particles encapsulate the protective structure, wherein the second vesicle or the second polycondensation polymer particles intervene on the boundary region between the oil phase and the second aqueous phase; and applying a substrate contained in the second aqueous phase to the enzyme to cause the enzymatic reaction, wherein the substrate is added in the second aqueous phase after the protective structure is dispersed in the second aqueous phase, or the protective structure is dispersed in the second aqueous phase in which the substrate is already present, and wherein, the protective structure comprises:
(a) the first polycondensation polymer particles and the second polycondensation polymer particles;
(b) the first vesicle and the second vesicle;
(c) the first polycondensation polymer particles and the second vesicle, or
(d) the first vesicle and the second polycondensation particles,
wherein,
when the protective structure comprises (a) the first polycondensation polymer particles and the second polycondensation polymer particles or (c) the first polycondensation polymer particles and the second vesicle, only the first polycondensation polymer particles intervene on the boundary region between the first aqueous phase and the oil phase,
when the protective structure comprises (d) the first vesicle and the second polycondensation particles, only the first vesicle intervenes on the boundary region between the first aqueous phase and the oil phase.

7. The enzymatic reaction method according to claim 6, wherein the first aqueous phase is composed of two or more aqueous sub-phases surrounded by the first vesicle or the first polycondensation polymer particles; the enzyme is composed of two or more enzymes; a first enzyme contained in a first aqueous sub-phase is different from a second enzyme contained in a second aqueous sub-phase; the protective structure is composed of two or more protective structures; and a first protective structure contains the first aqueous sub-phase and a second protective structure contains the second aqueous sub-phase.

8. The enzymatic reaction method according to claim 7, wherein the first enzyme contained in the first aqueous sub-phase has an activity to inhibit the second enzyme contained in the second aqueous sub-phase.

9. A method of producing a reaction product comprising:
forming a protective structure having water-in-oil emulsion structure surrounding an enzyme, wherein the protective structure comprises
    (a) (i) a first vesicle surrounding a first aqueous phase comprising the enzyme, wherein the first vesicle consists of a first amphiphilic substance which spontaneously forms vesicles, and the first vesicles has an average particle size of 8 to 500 nm, or
    (a) (ii) first polycondensation polymer particles having hydroxyl groups encapsulating the first aqueous phase comprising the enzyme;
    and
    (b) an oil phase being a different substance from the first vesicle and the first polycondensation polymer particles, wherein the first aqueous phase is dispersed in the oil phase as a discontinuous phase, wherein the first aqueous phase is dispersed in the oil phase while the first vesicle or the first polycondensation polymer particles encapsulate the first aqueous phase, wherein the first vesicle or the first polycondensation polymer particles intervene on the boundary region between the first aqueous phase and the oil phase;
forming a second vesicle encapsulating the protective structure or second polycondensation polymer particles encapsulating the protective structure, wherein the second vesicle is formed of a second amphiphilic substance which spontaneously forms vesicles, wherein the second polycondensation polymer particles have hydroxyl groups;
dispersing the protective structure as a discontinuous phase in a second aqueous phase to form a water-in-oil-in-water emulsion, wherein the protective structure is dispersed in the second aqueous phase while the second vesicle or the second polycondensation polymer particles encapsulate the protective structure, wherein the second vesicle or the second polycondensation polymer particles intervene on the boundary region between the oil phase and the second aqueous phase; and
applying a substrate contained in the second aqueous phase to the enzyme to cause a reaction between the substrate and the enzyme to produce the reaction product of the substrate, wherein the substrate is added in the second aqueous phase after the protective structure is dispersed in the second aqueous phase, or the protective structure is dispersed in the second aqueous phase in which the substrate is already present, and
wherein, the protective structure comprises:
(a) the first polycondensation polymer particles and the second polycondensation polymer particles;
(b) the first vesicle and the second vesicle;
(c) the first polycondensation polymer particles and the second vesicle, or
(d) the first vesicle and the second polycondensation particles,
wherein,
when the protective structure comprises (a) the first polycondensation polymer particles and the second polycondensation polymer particles or (c) the first polycondensation polymer particles and the second vesicle, only the first polycondensation polymer particles intervene on the boundary region between the first aqueous phase and the oil phase,
when the protective structure comprises (d) the first vesicle and the second polycondensation particles, only the first vesicle intervenes on the boundary region between the first aqueous phase and the oil phase.

10. A method of reducing the speed of an enzymatic reaction comprising
forming a protective structure having water-in-oil emulsion structure surrounding an enzyme, wherein the protective structure comprises
    (a) (i) a first vesicle surrounding a first aqueous phase comprising the enzyme, wherein the first vesicle consists of a first amphiphilic substance which spontaneously forms vesicles, and the first vesicles has an average particle size of 8 to 500 nm, or
    (a) (ii) first polycondensation polymer particles having hydroxyl groups encapsulating the first aqueous phase comprising the enzyme;
    and
    (b) an oil phase being a different substance from the first vesicle and the first polycondensation polymer particles, wherein the first aqueous phase is dispersed in the oil phase as a discontinuous phase, wherein the first aqueous phase is dispersed in the oil phase while the first vesicle or the first polycondensation polymer particles encapsulate the first aqueous phase, wherein the first vesicle or the first polycondensation polymer particles intervene on the boundary region between the first aqueous phase and the oil phase;
forming a second vesicle encapsulating the protective structure or second polycondensation polymer particles encapsulating the protective structure, wherein the second vesicle is formed of a second amphiphilic substance which spontaneously forms vesicles, wherein the second polycondensation polymer particles have hydroxyl groups;
dispersing the protective structure as a discontinuous phase in a second aqueous phase to form a water-in-oil-in-water emulsion, wherein the protective structure is dispersed in the second aqueous phase while the second vesicle or the second polycondensation polymer particles encapsulate the protective structure, wherein the second vesicle or the second polycondensation polymer particles intervene on the boundary region between the oil phase and the second aqueous phase;
applying a substrate contained in the second aqueous phase to the enzyme to cause a reaction between the substrate and the enzyme, wherein the substrate is added in the second aqueous phase after the protective structure is dispersed in the second aqueous phase, or the protective structure is dispersed in the second aqueous phase in which the substrate is already present; and reducing the speed of the enzymatic reaction by increasing the ratio of amount of the oil phase to the amount of the first aqueous phase in the protective structure surrounding the substance, wherein the ratio is adjusted prior to the step of applying the substrate to the enzyme, and wherein, the protective structure comprises:
(a) the first polycondensation polymer particles and the second polycondensation polymer particles;
(b) the first vesicle and the second vesicle;
(c) the first polycondensation polymer particles and the second vesicle, or
(d) the first vesicle and the second polycondensation particles,
wherein,
when the protective structure comprises (a) the first polycondensation polymer particles and the second polycondensation polymer particles or (c) the first polycondensation polymer particles and the second vesicle, only the first polycondensation polymer particles intervene on the boundary region between the first aqueous phase and the oil phase,
when the protective structure comprises (d) the first vesicle and the second polycondensation particles, only the first vesicle intervenes on the boundary region between the first aqueous phase and the oil phase.

11. The method of adjusting the speed of the enzymatic reaction according to claim 10, wherein the first aqueous phase is composed of two or more aqueous sub-phases surrounded by the first vesicle or the first polycondensation polymer particles; the enzyme is composed of two or more enzymes; a first enzyme contained in a first aqueous sub-phase is different from a second enzyme contained in a second aqueous sub-phase; the protective structure is composed of two or more protective structures; and a first protective structure contains the first aqueous sub-phase and a second protective structure contains the second aqueous sub-phase.

12. The method for adjusting the speed of the enzymatic reaction according to claim 11, wherein the first enzyme contained in the first aqueous sub-phase has an activity to inhibit the second enzyme contained in the second aqueous sub-phase.

13. A method of increasing the speed of an enzymatic reaction comprising
forming a protective structure having water-in-oil emulsion structure surrounding an enzyme, wherein the protective structure comprises
(a) (i) a first vesicle surrounding a first aqueous phase comprising the enzyme, wherein the first vesicle consists of a first amphiphilic substance which spontaneously forms vesicles, and the first vesicles has an average particle size of 8 to 500 nm, or
(a) (ii) first polycondensation polymer particles having hydroxyl groups encapsulating the first aqueous phase comprising the enzyme; and (b) an oil phase being a different substance from the first vesicle and the first polycondensation polymer particle, wherein the first aqueous phase is dispersed in the oil phase as a discontinuous phase, wherein the first aqueous phase is dispersed in the oil phase while the first vesicle or the first polycondensation polymer particles encapsulate the first aqueous phase, wherein the first vesicle or the first polycondensation polymer particles intervene on the boundary region between the first aqueous phase and the oil phase;

forming a second vesicle encapsulating the protective structure or second polycondensation polymer particles encapsulating the protective structure, wherein the second vesicle is formed of a second amphiphilic substance which spontaneously forms vesicles, wherein the second polycondensation polymer particles have hydroxyl groups;

dispersing the protective structure as a discontinuous phase in a second aqueous phase to form a water-in-oil-in-water emulsion, wherein the protective structure is dispersed in the second aqueous phase while the second vesicle or the second polycondensation polymer particles encapsulate the protective structure, wherein the second vesicle or the second polycondensation polymer particles intervene on the boundary region between the oil phase and the second aqueous phase;

applying a substrate contained in the second aqueous phase to the enzyme to cause a reaction between the substrate and the enzyme, wherein the substrate is added in the second aqueous phase after the protective structure is dispersed in the second aqueous phase, or the protective structure is dispersed in the second aqueous phase in which the substrate is already present; and increasing the speed of the enzymatic reaction by decreasing the ratio of amount of the oil phase to the amount of the first aqueous phase in the protective structure surrounding the substance, wherein the ratio is adjusted prior to the step of applying the substrate to the enzyme, wherein, the protective structure comprises:
(a) the first polycondensation polymer particles and the second polycondensation polymer particles;
(b) the first vesicle and the second vesicle;
(c) the first polycondensation polymer particles and the second vesicle, or
(d) the first vesicle and the second polycondensation particles,
wherein,
when the protective structure comprises (a) the first polycondensation polymer particles and the second polycondensation polymer particles or (c) the first polycondensation polymer particles and the second vesicle, only the first polycondensation polymer particles intervene on the boundary region between the first aqueous phase and the oil phase,
when the protective structure comprises (d) the first vesicle and the second polycondensation particles, only the first vesicle intervenes on the boundary region between the first aqueous phase and the oil phase.

\* \* \* \* \*